US011413104B2

(12) United States Patent
Nichogi

(10) Patent No.: US 11,413,104 B2
(45) Date of Patent: Aug. 16, 2022

(54) MEDICAL MANIPULATOR SYSTEM AND METHOD FOR OPERATING MEDICAL MANIPULATOR SYSTEM

(71) Applicant: OLYMPUS CORPORATION, Tokyo (JP)

(72) Inventor: Masao Nichogi, Koza-gun (JP)

(73) Assignee: OLYMPUS CORPORATION, Tokyo (JP)

( * ) Notice: Subject to any disclaimer, the term of this patent is extended or adjusted under 35 U.S.C. 154(b) by 426 days.

(21) Appl. No.: 16/654,148

(22) Filed: Oct. 16, 2019

(65) Prior Publication Data

US 2020/0038129 A1 Feb. 6, 2020

Related U.S. Application Data

(63) Continuation of application No. PCT/JP2017/017141, filed on May 1, 2017.

(51) Int. Cl.
*A61B 34/00* (2016.01)
*A61B 17/00* (2006.01)
(Continued)

(52) U.S. Cl.
CPC ........ *A61B 34/74* (2016.02); *A61B 17/00234* (2013.01); *B25J 13/08* (2013.01);
(Continued)

(58) Field of Classification Search
CPC .............. A61B 34/74; A61B 17/00234; A61B 2017/00022; A61B 2017/00292; A61B 34/70; A61B 34/76; A61B 2017/00336; A61B 2090/064; A61B 2090/067; A61B 34/37; B25J 13/08; A61M 25/0113; A61M 25/0662

See application file for complete search history.

(56) References Cited

U.S. PATENT DOCUMENTS

2010/0292566 A1  11/2010  Nagano et al.
2015/0272684 A1  10/2015  Tsusaka et al.
2019/0357988 A1* 11/2019  Abbott ................... A61B 34/35

FOREIGN PATENT DOCUMENTS

EP      3147085 A1    3/2017
JP   2009-162746 A    7/2009
(Continued)

OTHER PUBLICATIONS

International Search Report dated Jul. 25, 2017 issued in PCT/JP2017/017141.

*Primary Examiner* — Richard G Louis
(74) *Attorney, Agent, or Firm* — Scully, Scott, Murphy & Presser, P.C.

(57) ABSTRACT

A medical manipulator system including: a treatment tool unit including an arm portion having an arm with a joint and an end effector attached to the arm; an overtube having a lumen through which the treatment tool unit is inserted; a drive source configured to generate a drive force for driving the joint; a controller configured to generate an operation signal for operating the drive source; and a detector configured to detect friction generated between an inner surface of the lumen and the treatment tool unit. The controller calculates a correction amount for adjusting the operation signal based on the detected friction.

20 Claims, 9 Drawing Sheets

(51) Int. Cl.
 *B25J 13/08* (2006.01)
 *A61M 25/01* (2006.01)
 *A61M 25/06* (2006.01)

(52) U.S. Cl.
 CPC ............... *A61B 2017/00022* (2013.01); *A61B 2017/00292* (2013.01); *A61M 25/0113* (2013.01); *A61M 25/0662* (2013.01)

(56) References Cited

FOREIGN PATENT DOCUMENTS

JP          4580973 B2    11/2010
JP     2015-163413 A       9/2015
JP     2015-198924 A      11/2015

* cited by examiner

MEDICAL MANIPULATOR SYSTEM AND METHOD FOR OPERATING MEDICAL MANIPULATOR SYSTEM

CROSS REFERENCE TO RELATED APPLICATIONS

This application is a continuation application based on a PCT Patent Application No. PCT/JP2017/017141, filed on May 1, 2017, the content of which is incorporated herein by reference.

BACKGROUND

Technical Field

The present invention relates to a medical manipulator system and method for operating a medical manipulator system.

Background Art

Conventionally, a medical manipulator operated by an operator in a state in which observation means and a plurality of treatment tools are inserted into the body is known.

Generally, the observation means and the treatment tool have a long insertion portion. When the observation means or the treatment tool includes an active drive portion such as a joint or a bending portion, a wire or the like for transmitting the driving force to the active drive portion is inserted into the insertion portion.

When the medical manipulator is introduced into the digestive tract or the like, the insertion portion of the observation means and the treatment tool meanders along the meandering digestive tract and the like in the body. When the insertion portion meanders, the path length of the wire or the like in the insertion portion changes or the wire or the like extends, and the correspondence relationship between the driving amount of the wire or the like and the driving amount of the active driving portion changes. As a result, the drive accuracy of the active drive site is lowered, and problems such as the active drive site not operating as intended by the operator occur.

In relation to the above problems, a treatment tool system described in Japanese Patent (Granted) Publication No. 4580973 has been proposed. The treatment tool system includes an endoscope and a treatment tool having a joint. The joint is electrically driven by the control means. The treatment tool system includes detection means for always detecting the bending state of the endoscope insertion portion, and the control means generates a drive signal of the joint while reflecting the bending state of the endoscope insertion portion detected by the detection means. Thereby, the operation signal of the treatment tool is adjusted according to the bending state of the endoscope insertion portion, and the treatment tool operates smoothly.

SUMMARY

A medical manipulator system includes: a treatment tool unit including an arm portion having an arm with a joint and an end effector attached to the arm; an overtube having a lumen through which the treatment tool unit is inserted; a drive source configured to generate a drive force for driving the joint; a controller configured to generate an operation signal for operating the drive source, and a detector configured to detect friction generated between an inner surface of the lumen and the treatment tool unit. The controller calculates a correction amount for adjusting the operation signal based on the detected friction.

The treatment tool unit may have a motor unit in which the drive source is disposed, and a flexible connection portion disposed between the arm portion and the motor unit, and the detector may detect a force generated between the connection portion and the motor unit by the friction.

The medical manipulator system may further include: a mounting portion to which the treatment tool unit is attached and configured to advance and retreat the treatment tool unit relative to the overtube. The detector may detect a force generated between the treatment tool unit and the mounting portion by the friction.

The medical manipulator system may further include: a speed sensor configured to be able to detect a moving speed of the treatment tool unit connected to the mounting portion. The controller may calculate the correction amount based on the detected friction and the moving speed detected by the speed sensor.

A method for operating a medical manipulator system including a treatment tool unit having an arm portion including an arm having a joint and an end effector attached to the arm, an overtube having a lumen through which the treatment tool unit is inserted, a drive source configured to generate a driving force for driving the joint, and a controller configured to generate an operation signal for operating the drive source, the method comprising: moving the treatment tool unit relative to the overtube; detecting friction generated between an inner surface of the lumen and the treatment tool unit by the relative movement; and calculating a correction amount for correcting the operation signal based on the detected friction.

DETAILED DESCRIPTION OF THE PREFERRED EMBODIMENTS

A first embodiment of the present invention will be described with reference to FIGS. 1 to 8.

Figure 1:
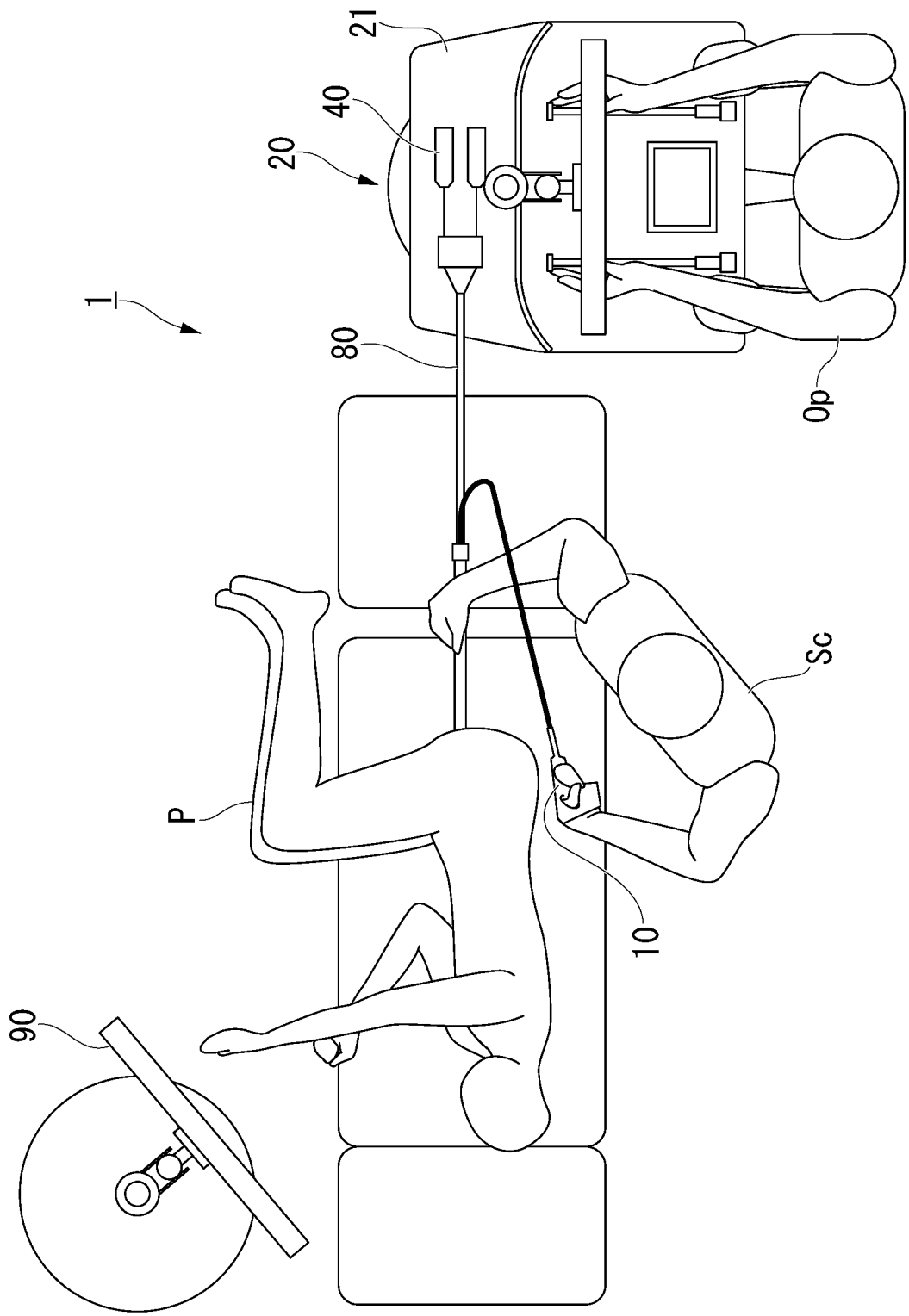
FIG. 1 is a view showing a medical manipulator system according to a first embodiment of the present invention.

FIG. 1 is a view showing a medical manipulator system (hereinafter simply referred to as "system") 1 of the present embodiment. The system 1 includes an endoscope 10 for observing the inside of a patient P, a medical manipulator (hereinafter simply referred to as a "manipulator") 20 for performing treatment in the body of the patient P, and a flexible overtube 80 through which the endoscope 10 and the manipulator 20 are inserted.

The endoscope 10 can be appropriately selected from various known configurations in consideration of performance, use, and the like.

Although not shown, the overtube 80 has a first lumen through which the endoscope 10 is inserted and a second lumen through which the manipulator 20 is inserted. The overtube 80 can also be appropriately selected from various known configurations in consideration of dimensions and the like. If an overtube having a configuration having a curved portion on the distal end side is used, it is easy to reach a target site to be treated.

The manipulator 20 includes a console 21 operated by the operator Op, and a treatment tool unit 40 attached to the console 21.

Figure 2:
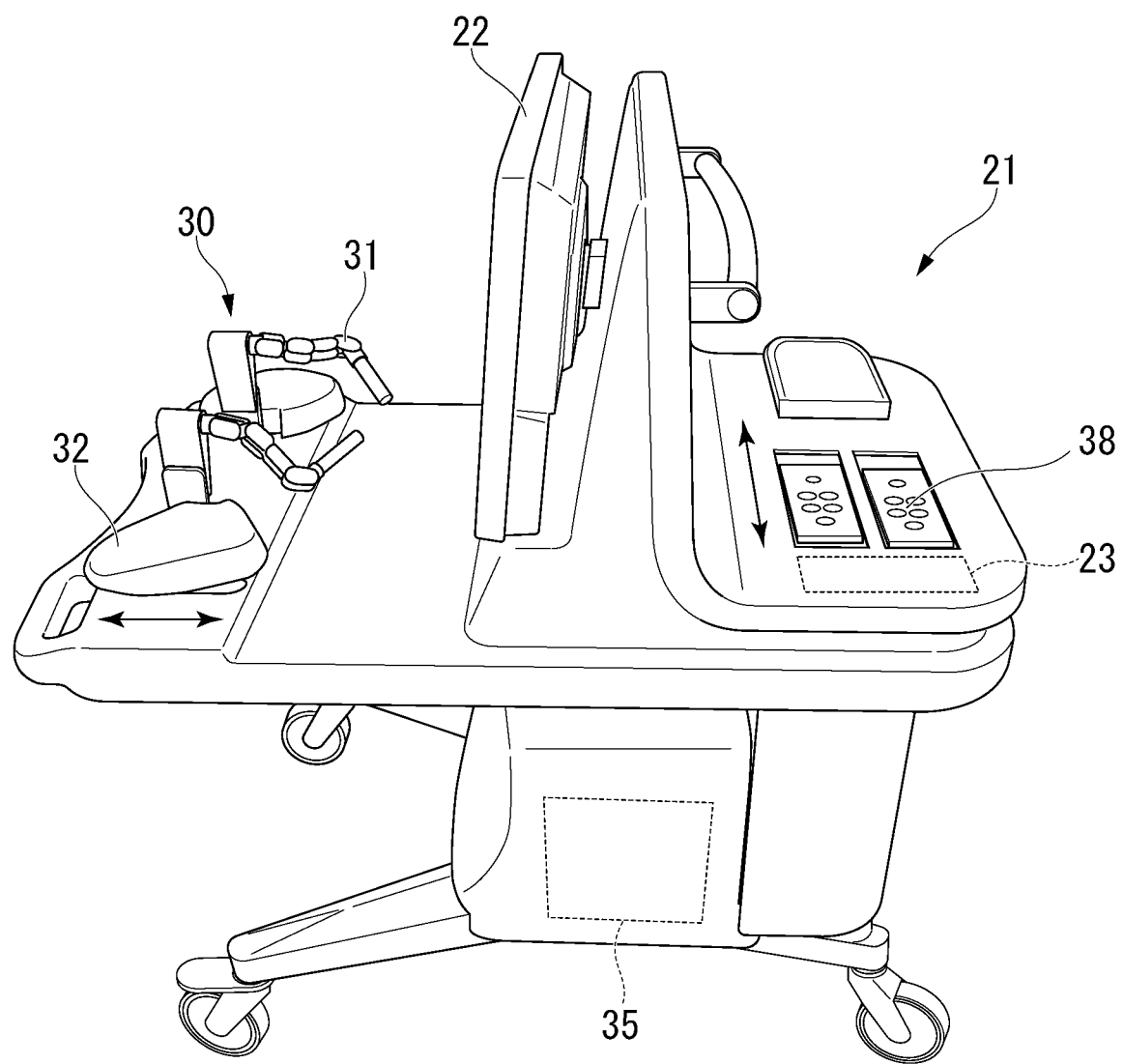
FIG. 2 is a view showing a console in the medical manipulator system.

FIG. 2 is a view showing the console 21. The console 21 has an operation portion 30 for operation input by the operator Op, a control portion (controller) 35 for operating the treatment tool unit 40 based on an output from the operation portion 30, a mounting portion (advancement/retraction drive portion) 38 to which the treatment tool unit 40 is attached, and a monitor 22.

The monitor 22 is connected to the endoscope 10 and displays an image acquired by the endoscope 10.

Figure 3:
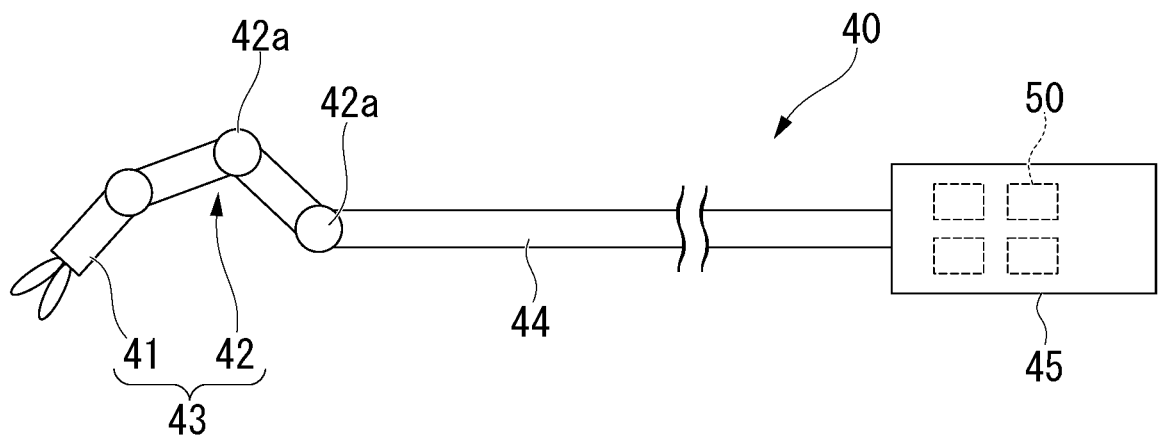
FIG. 3 is a schematic view showing a treatment tool unit in the medical manipulator system.

FIG. 3 is a view schematically showing the treatment tool unit 40. The treatment tool unit 40 includes an arm portion 43 having a treatment tool (end effector) 41 and an arm 42 to which the treatment tool 41 is attached, and a motor unit 45 for driving the treatment tool 41 and the arm 42. An area between the arm portion 43 and the motor unit 45 is a flexible connection portion 44.

Figure 4:
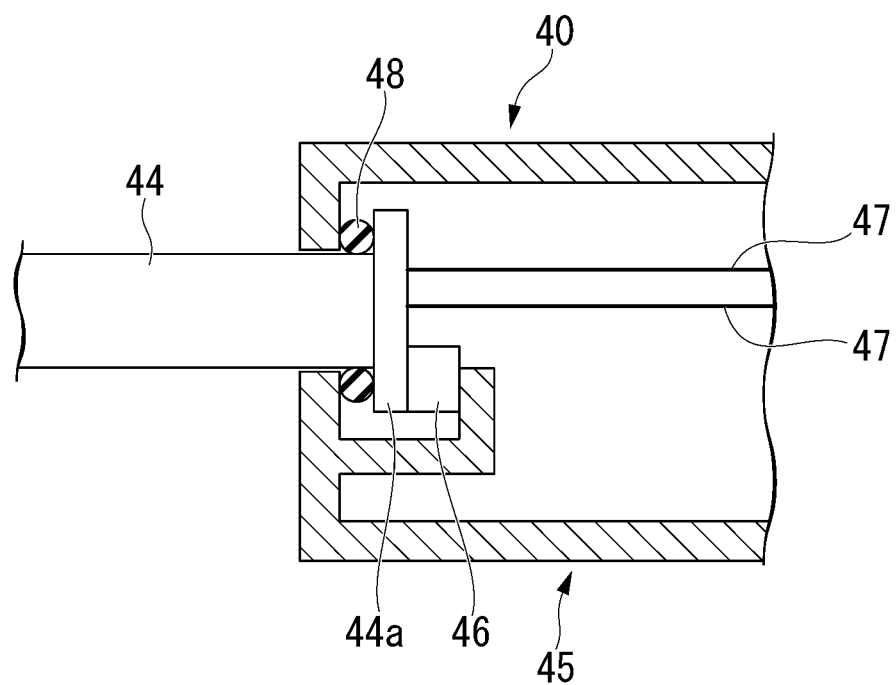
FIG. 4 is a partial cross-sectional view of the treatment tool unit.

FIG. 4 is a cross-sectional view showing a connection area between the connection portion 44 and the motor unit 45 in the treatment tool unit 40. In the motor unit 45, a plurality of drive sources 50 corresponding to the plurality of joints 42a provided on the arm 42 are disposed. A plurality of transmission members 47 for transmitting the driving force from the respective drive sources 50 to the corresponding joints 42a are connected to the corresponding joints 42a through the inside of the connection portion 44.

A motor can be exemplified as the drive source 50, and a wire can be exemplified as the transmission member 47.

A flange 44a is provided at the proximal end of the connection portion 44, and the connection portion 44 is configured not to come off the motor unit 45. A strain sensor as a detector (friction detection portion) 46 is disposed behind the flange 44a so as to be in contact with the flange 44a and not to interfere with the transmission member 47. In the motor unit 45, a bearing 48 is disposed in front of the flange 44a. The bearing 48 has a function of reducing the friction caused by the relative movement of the connection portion 44 and the motor unit 45 that will be described later.

Figure 5:
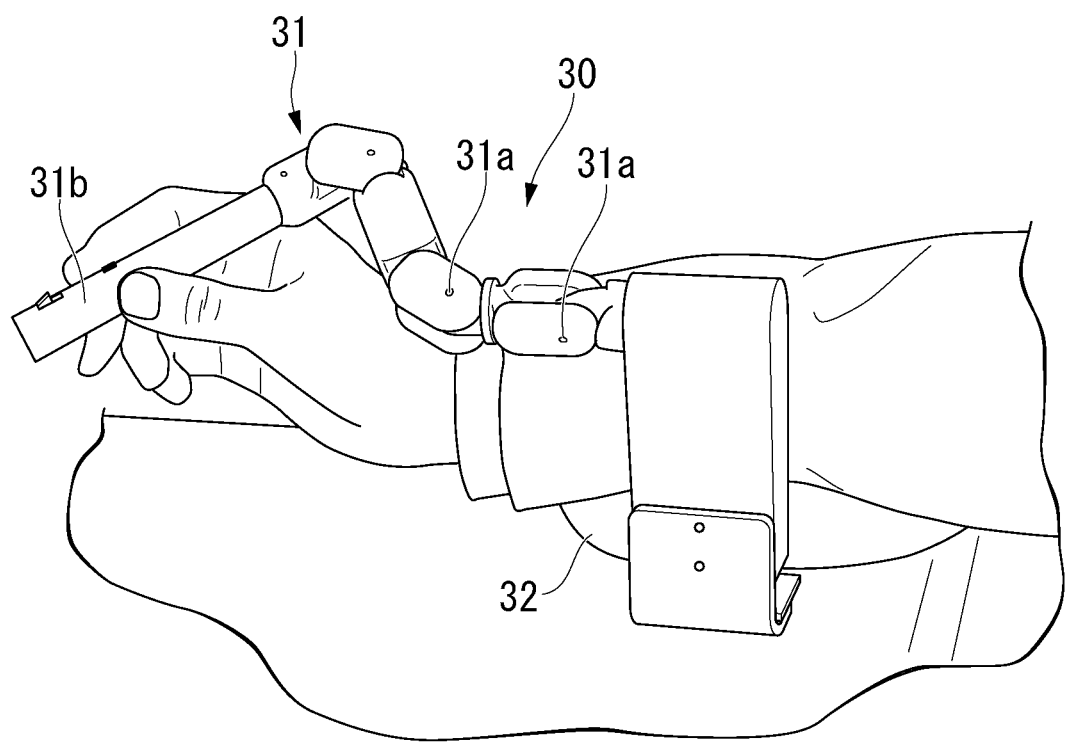
FIG. 5 is a diagram showing an operation portion in the console.

FIG. 5 is a view showing the operation portion 30 of the console 21. The operation portion 30 includes an operation arm 31 used for operation input to the arm portion 42 and a base portion 32 to which the operation arm 31 is attached.

The operation arm 31 has a plurality of joints 31a. The number of joints 31a and the number of joints 42a of the arm 42 are equal, and the aspect of the rotation axis of each joint is the same. Each joint 31a is provided with an encoder or the like (not shown) that enables a rotation angle to be detected. When the operator Op operates the operation arm 31 to make the shape into an arbitrary shape, the control portion 35 generates the operation signals of the plurality of drive sources 50 corresponding to the joints 42a based on the detection values of the encoders attached to the joints 31a. When the drive source 50 is operated by the operation signal, each joint 42a of the arm 42 is driven, and the shape of the arm portion 43 becomes a shape similar to the shape of the operation arm 31.

A treatment operation portion 31b for operating the treatment tool 41 is provided at the distal end of the operation arm 31. The specific mode of the treatment operation portion 31b can be appropriately set according to the configuration of the treatment tool 41 and the like. For example, when the treatment tool 41 is a grasping forceps, the treatment operation portion 31b may have a structure equivalent to that of the grasping forceps. When the treatment tool 41 is a knife that is used by being energized, the treatment operation portion 31b may be configured to have a button for switching the energization on/off.

The base portion 32 is attached so as to be movable relative to the console 21. When the base portion 32 is moved relative to the console 21, the mounting portion 38 moves relative to the console 21. Thereby, the treatment tool unit 40 attached to the mounting portion 38 can be moved relative to the console 21.

Figure 6:
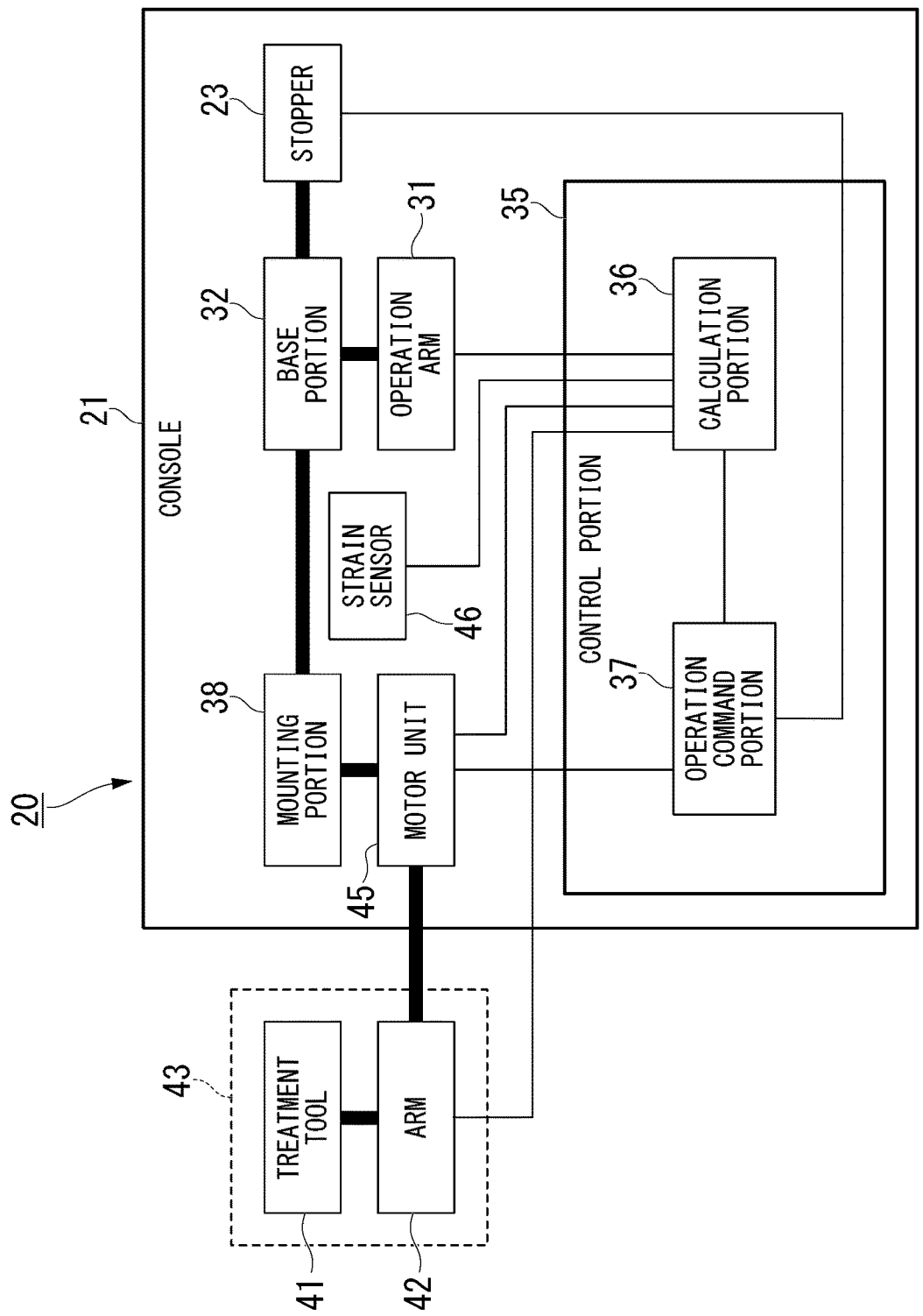
FIG. 6 is a functional block diagram of the medical manipulator in the medical manipulator system.

FIG. 6 is a functional block diagram of the manipulator 20 in a state where the treatment tool unit 40 is attached to the console 21. The monitor 22 is omitted in FIG. 6. In FIG. 6, thick lines connecting the respective configurations represent physical couplings capable of transmitting power, and thin lines connecting the respective configurations represent logical couplings capable of transmitting and receiving signals.

In the manipulator 20 of the present embodiment, the base portion 32 and the mounting portion 38 are physically connected by, for example, a belt, a chain, or the like. Therefore, when the base portion 32 is moved relative to the console 21, the mounting portion 38 moves relative to the console 21 in conjunction with the base portion 32. At this time, the operation arm 31 moves with the base portion 32, and the motor unit 45 attached to the mounting portion 38 also moves with the mounting portion 38.

As described above, the motor unit 45 is physically coupled to the arm portion 43 by the transmission member 47. The treatment tool 41 is also connected to the drive source 50 by the transmission member as needed.

The control portion 35 includes a calculation portion 36 that performs various calculations and determinations, and an operation command portion 37 that is logically connected to the calculation portion 36 and operates each element of the manipulator 20 according to the output of the calculation portion 36.

The calculation portion 36 is logically connected to the operation arm 31, the arm 42, the motor unit 45, and the strain sensor 46. The operation command portion 37 is logically connected to the motor unit 45, and is configured to be able to operate each drive source 50 of the motor unit 45 by transmitting an operation signal.

The hardware configuration of the control portion 35 can be configured by combining a processor, a logic circuit, a memory, a circuit for connecting them, and the like. The hardware configuration may include two or more of the elements described above, or may not include one of a processor and a logic circuit. In still another aspect, the control portion 35 may include two or more independent housings, and the respective housings may be connected by a network circuit (including wireless communication).

The operation at the time of use of the system 1 configured as described above will be described using an example of treating the large intestine. As shown in FIG. 1, the system 1 is operated by at least two persons, including an operator Op who operates the console 21 and a scopist Sc who operates the overtube 80 and the endoscope 10.

Figure 7:
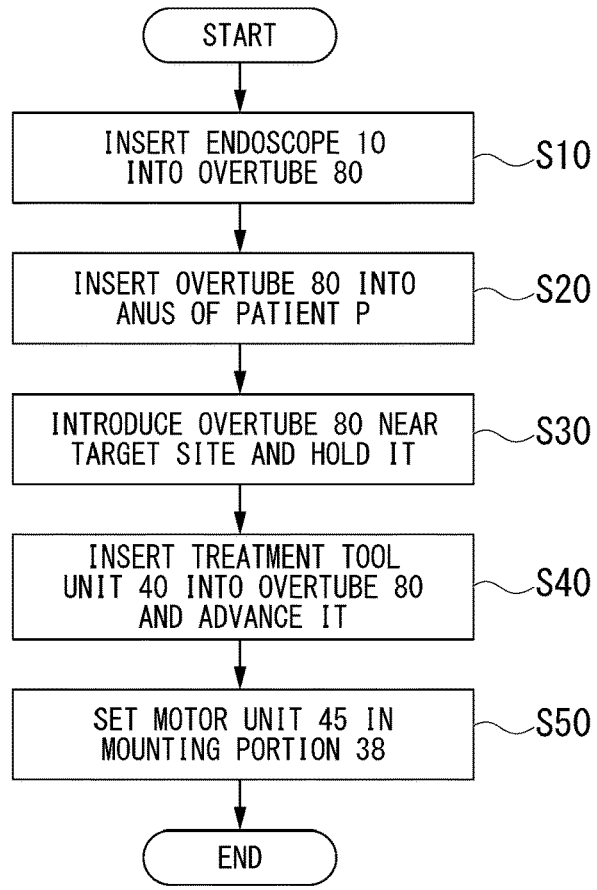
FIG. 7 is a flowchart showing the flow of a preparation operation in the medical manipulator system.

FIG. 7 is a flowchart showing the flow of the preparation operation before using the system 1.

First, in step S10, the scopist Sc inserts the endoscope 10 into the first lumen of the overtube 80.

Subsequently, in step S20, the scopist Sc inserts the overtube 80 in which the endoscope 10 is inserted into the anus of the patient P.

Subsequently, in step S30, the scopist Sc advances the overtube 80 in the large intestine while observing the image acquired by the endoscope 10 with the second monitor 90 (see FIG. 1), and introduces the overtube 80 in which the endoscope 10 is inserted into the vicinity of the target site. While receiving instructions from the operator Op, the scopist Sc finely adjusts the endoscope 10 and the overtube 80 to determine the field of view for capturing the target site, and holds the endoscope 10 and the overtube 80.

By the operation of step S30, the overtube 80 and the first and second lumens formed in the overtube 80 are curved following the movement of the large intestine from the anus to the target site. The curved shape of the overtube 80 and each of the lumens is maintained by the scopist Sc holding the endoscope 10 and the overtube 80, so that it does not change significantly until the field of vision or the target site is changed.

In the subsequent step S40, the treatment tool unit 40 is inserted into the second lumen of the overtube 80 from the arm portion 43 side. The treatment tool unit 40 is advanced toward the distal end side of the overtube 80 through the curved second lumen. The treatment tool unit 40 is advanced until the treatment tool 41 is near the distal end opening of the second lumen. Since it may be difficult to see this state from the image of the endoscope 10, the connection portion 44 may be provided with a marker or the like corresponding to this state as necessary.

At this time, the operation arm 31 of the console 21 is substantially linear so that it has substantially the same shape as the arm portion 43.

In the subsequent step S50, the motor unit 45 of the treatment tool unit 40 is set to the mounting portion 38. When the motor unit 45 is set in the mounting portion 38, the motor unit 45 and the control portion 35 are logically connected.

The operations of steps S40 and S50 may be performed by the operator Op, or may be performed by an assistant or the like different from the operator.

Thus, the preparation operation is completed.

When the preparation operation is completed, the system 1 can operate the manipulator 20. In this operable state, the overtube 80 and each lumen are curved following the movement of the large intestine as described above. Therefore, the connection portion 44 inserted in the second lumen is also curved in the second lumen following the curved second lumen. When the transmission member 47 inserted into the connection portion 44 is moved back and forth in the operable state, the transmission member 47 comes into contact with the inner surface of the connection portion 44 to generate friction more often as compared with the case where the connection portion 44 is in the straight state. As a result, the responsiveness of the arm portion 43 to the operation of the console 21 is lower than when the connection portion 44 is in the linear state. More specifically, the sensitivity, which is the ratio of the drive amount of the joint 42$a$ to the drive amount of the drive source 50, decreases, or the value of the dead zone indicated as the drive amount of the drive source 50 after the direction of the drive amount changes in the drive source until the arm portion actually starts driving may increase.

In order to suppress the decrease in responsiveness or to improve the decreased responsiveness again, it is necessary to adjust the operation signal by a correction amount according to the state of the manipulator at that time, more specifically, the bending state of the connection portion 44. The inventor paid attention to the amount of friction generated between the connection portion 44 and the second lumen as a parameter for determining the amount of correction.

That is, the positional relationship between the transmission member 47 traveling in the connection portion 44 and the inner surface of the connection portion 44 is similar to the positional relationship between the connection portion 44 traveling in the second lumen and the inner surface of the second lumen, and the manner of occurrence of friction between the two members is generally the same. In addition, the friction generated between the connection portion and the transmission member and the friction generated between the second lumen and the connection portion both increase in accordance with the total bending angle (the degree of bending of the soft shape) which is increased as it is inserted deep in the intestinal tract. That is, as the total bending angle increases, the friction also increases, and as a result, the elongation of the transmission member also increases. Therefore, the correction amount becomes large.

Therefore, the system 1 of the present embodiment is configured so that the amount of friction generated between the connection portion 44 and the second lumen is used as a substitute parameter of the amount of friction generated between the transmission member 47 and the connection portion 44, and the control portion 35 calculates the correction amount of the operation signal based on the friction generated between the connection portion 44 and the second lumen.

Figure 8:
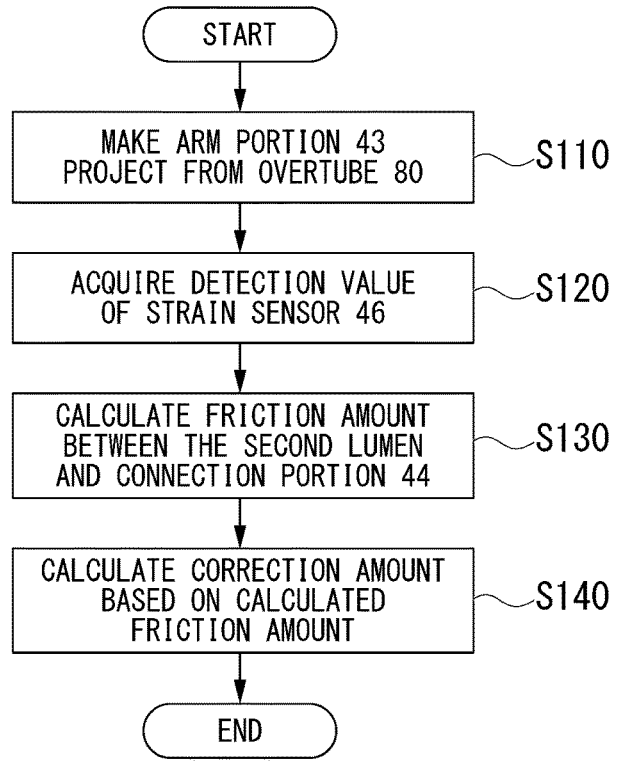
FIG. 8 is a flowchart showing a flow of correction amount calculation in the medical manipulator system.

FIG. 8 is a flowchart showing the flow of correction amount calculation in the system 1.

First, in step S110, when the operator Op moves the base portion 32 forward while holding the operation arm 31, the mounting portion 38 and the motor unit 45 interlock with each other, and the treatment tool unit 40 moves to the distal end side of the overtube 80 (relative movement step). As a result, the arm portion 43 protrudes from the overtube 80.

At this time, if friction occurs between the connection portion 44 and the second lumen, the advancing amount of the connection portion 44 becomes smaller than the advancing amount of the motor unit 45. As a result, the proximal end of the connection portion 44 located in the motor unit 45 retracts with respect to the motor unit 45, and the flange portion 44$a$ presses the strain sensor 46 (friction detection step). That is, as the amount of friction generated between the connection portion 44 and the second lumen increases, the force generated between the connection portion 44 and the motor unit 45 increases, and the strength with which the flange portion 44$a$ presses the strain sensor 46 grows.

In the subsequent step S120, the calculation portion 36 acquires a detection value (friction parameter) reflecting the amount of friction generated between the connection portion 44 and the second lumen from the strain sensor 46 (friction parameter acquisition step).

Furthermore, in step S130, the calculation portion 36 calculates the amount of friction generated between the second lumen and the connection portion 44 based on the acquired detected value (a friction amount calculation step). The specific method for calculating the amount of friction can be set as appropriate. For example, it is possible to exemplify a method such as substituting the acquired value of the friction parameter into the calculation formula derived by a preliminary experiment or the like, or referring to a table in which the value of the friction parameter and the friction amount are associated.

In the following step S140, the calculation portion 36 calculates a correction amount for adjusting the operation signal based on the friction amount calculated in step S130 (correction amount calculation step). The specific method for calculating the correction amount can be set as appropriate, and the method using a calculation formula and the method using a table can be exemplified as in the case of the method of calculating the friction amount.

Thus, the correction amount is calculated.

Thereafter, when the operator Op operates the operation arm 31, the output value of the encoder attached to each joint 31a changes.

The calculation portion 36 generates an adjusted operation signal based on the output value of each encoder received from the operation arm 31 at a predetermined interval (for example, several tens of milliseconds) and the calculated correction amount, and transmits it to the operation command portion 37. When the operation command portion 37 transmits the adjusted operation signal to each drive source 50 of the motor unit 45, each drive source 50 is driven based on the operation signal. As a result, the arm portion 43 is responsively controlled to be responsive so as to maintain a similar shape with respect to the operation arm 31.

The operator Op can perform a desired treatment on the target site by appropriately operating the operation arm 31 and the treatment operation portion 31b while confirming the image of the target site displayed on the monitor 22.

As described above, according to the system 1 of the present embodiment and the operation method of the medical manipulator system executed by the system 1, the amount of friction generated between the connection portion 44 and the overtube 80 is calculated based on the detection of the strain sensor 46, and the amount of correction based on the amount of friction is calculated. Furthermore, since the drive source 50 of the motor unit 45 is driven by the operation signal adjusted based on the calculated correction amount, even if the overtube 80 is curved or meanders in the body of the patient P, the arm portion 43 can be operated with responsiveness to the operation of the console 21 by the operator Op.

Moreover, since it is not necessary to provide an encoder or the like in the arm portion 43, a drop in the responsiveness can be suppressed without preventing the diameter reduction of the arm portion 43.

Furthermore, since the strain sensor 46 is disposed in the motor unit 45 which is always located outside the body when the system 1 is used, the strain sensor 46 does not have to be extremely small. Therefore, a general-purpose sensor can be applied without any problem, and the influence on the manufacturing cost of the treatment tool unit 40 is small.

In addition, since the bearing 48 is disposed in the motor unit 45, the friction when the connection portion 44 and the motor unit 45 move relative to each other is reduced. As a result, it is possible to suppress the decrease in accuracy of the detection value of the strain sensor 46.

In the system 1 of the present embodiment, the timing of the correction amount calculation can be set as appropriate. For example, the correction amount may be calculated at the start of use of the system 1, and the operator Op may not be permitted to start the procedure until it is calculated. In addition, in consideration of the case where the treatment target site is changed, the system 1 may be configured so that the operator Op performs a predetermined operation, and the correction amount can be calculated again at an arbitrary timing so that the correction amount can be updated.

The friction detection portion is not limited to the strain sensor, and a force sensor or the like may be used.

A second embodiment of the present invention will be described with reference to FIGS. 9 to 11. The present embodiment differs from the first embodiment in the configuration of the treatment tool unit and the console. In the following description, the same reference numerals are assigned to components common to those described above, and redundant description will be omitted.

Figure 9:
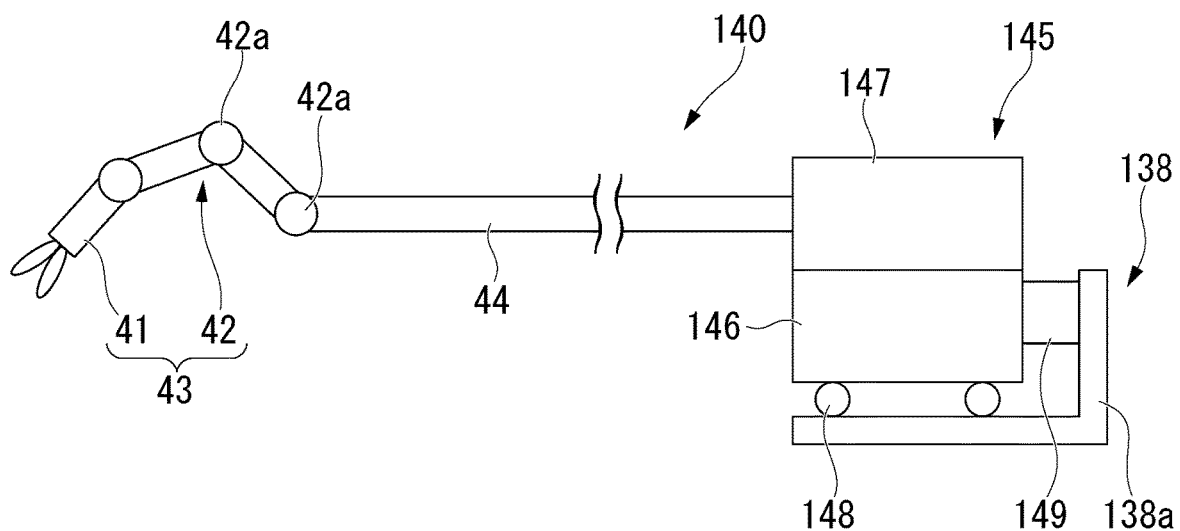
FIG. 9 is a schematic view showing a treatment tool unit in a medical manipulator system according to a second embodiment of the present invention.

FIG. 9 is a schematic view showing the treatment tool unit 140 in the system of the present embodiment. The motor unit 145 of the treatment tool unit 140 includes a first housing 146 disposed on the mounting portion 138 and a second housing 147 to which the connection portion 44 is connected.

Inside the first housing 146, a plurality of drive sources 50 (not shown) are disposed. A caster 148 is attached to the lower part of the first housing 146.

Inside the second housing 147, a plurality of pulleys (not shown) to which the transmission member 47 is connected are disposed. Unlike the first embodiment, the proximal end portion of the connection portion 44 is connected to the second housing 147 so as not to move relative to the second housing 147.

The upper surface of the mounting portion 138 is flat and smooth, and is configured so that, when the first housing 146 disposed on the mounting portion 138 moves relative to the mounting portion 138, almost no friction occurs between the two. Behind the mounting portion 138, there is provided a wall portion 138a which rises substantially perpendicularly to the upper surface, and a rear portion of the first housing 146 and the wall portion 138a are connected by a force sensor as a detector (friction detecting portion) 149.

The second housing 147 is configured to be attachable to and detachable from the first housing 146. When the second housing 147 is attached to the first housing 146, the drive shaft of the drive source 50 and the rotary shaft of the pulley are connected, and the pulley can be rotated by the drive source 50 to drive the joint 42a.

The force sensor 149 is logically connected to the calculation portion 36.

The operation at the time of use of the system of the present embodiment provided with the treatment tool unit 140 and the mounting portion 138 configured as described above will be described.

The preparation operation is substantially the same as that of the first embodiment except that the second housing 147 is mounted on the first housing 146 disposed on the mounting portion 138 in step S50.

In step S110, when friction occurs between the connection portion 44 and the second lumen, the first housing 146 to which the second housing 147 is connected cannot sufficiently follow the movement of the mounting portion 138. As a result, a force is generated between the first housing 146 and the mounting portion 138 in a direction to retract the first housing 146 with respect to the mounting portion 138, and the force sensor 149 is pressed by the first housing 146. The pressing force is detected by the force sensor 149.

In the friction parameter acquisition step of step S120, the detection value of the force sensor 149 is acquired instead of the detection value of the strain sensor 46. The other points are the same as in the first embodiment.

Also, according to the system of the present embodiment, as in the first embodiment, even if the overtube 80 is curved or meanders in the body of the patient P, the arm portion 43 can be operated with responsiveness to the operation of the console 21 by the operator Op.

Furthermore, since the force sensor 149 that functions as a friction detection portion is provided outside the motor unit 145, the manufacturing cost can be reduced when the treatment tool unit 140 is disposable. In addition, even when the treatment tool unit 140 is sterilized and repeatedly used, the friction detection portion is not required to have sterilization resistance, so the degree of freedom in selecting the mechanism used as the friction detection portion is high.

Figure 10A:
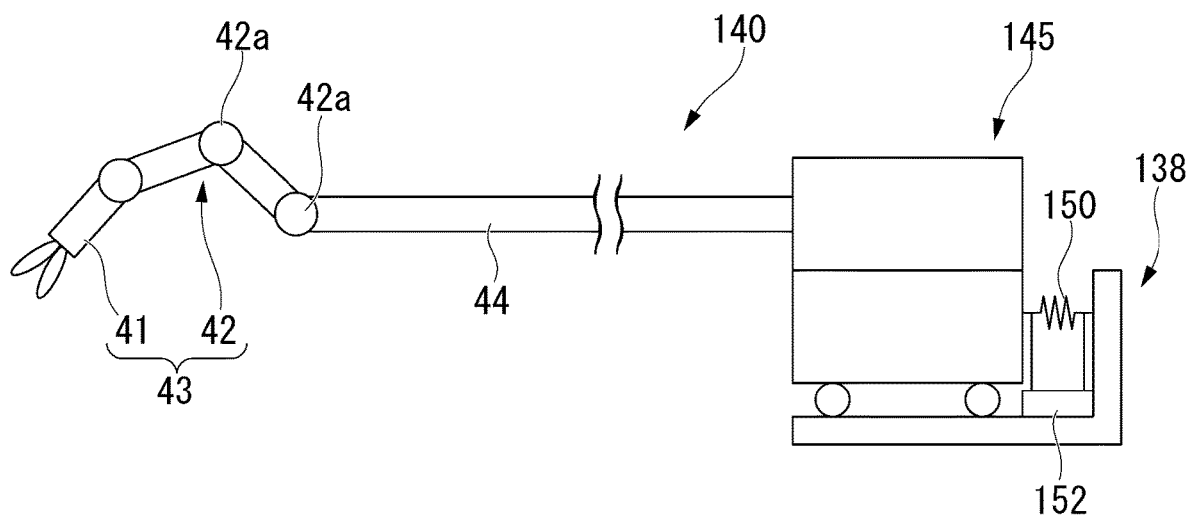
FIGS. 10A and 10B are views each showing a part of a modification of the medical manipulator system.

In the present embodiment, as in the modification shown in FIG. 10A, a configuration in which a spring 150 is provided instead of the force sensor 149 may be used. In this case, a configuration in which the displacement amount of the spring 150 can be measured by an encoder as a detector (friction detection portion) 152, a laser (not shown), or the like is adopted. Thus, the force acting on the spring 150 can be calculated based on the spring constant and the displacement amount of the spring 150, and can be acquired as a friction parameter.

In the above-described encoder, various methods such as a resistance method, a magnetic method, an optical method, and the like can be applied.

Figure 10B:
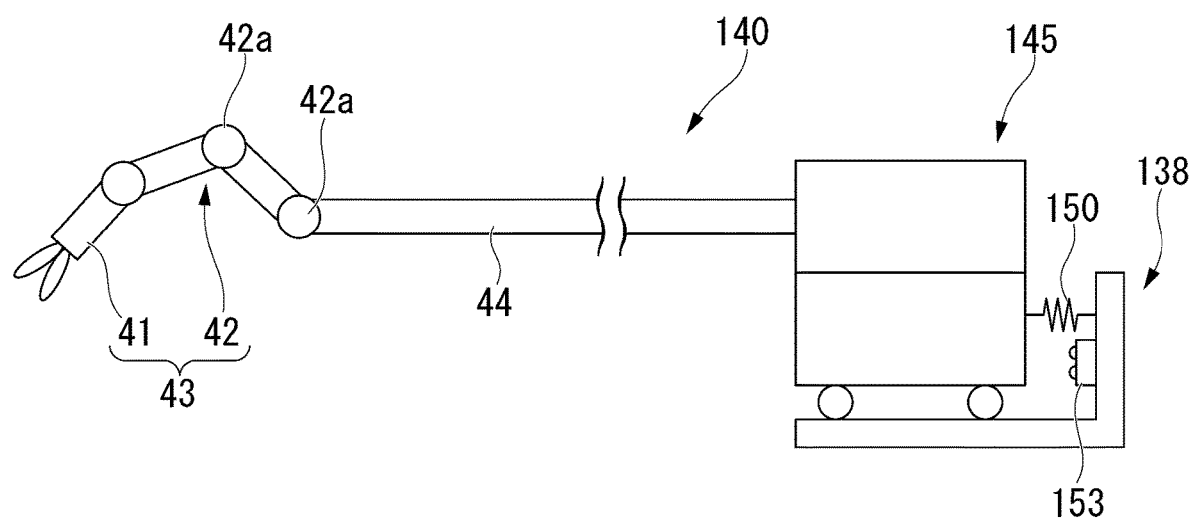

FIG. 10B shows an example using a laser measuring instrument as the encoder 152. In this case, the laser measuring instrument 153 measures the amount of movement of the motor unit 145 from the initial position. The measurement result of the laser measuring instrument 152 is converted to the amount of displacement of the spring 150. Then, the force acting on the spring 150 can be calculated based on the spring constant of the spring 150 and the calculated displacement amount, and can be acquired as the friction parameter.

As another means for measuring the amount of displacement of the spring 150, a configuration in which the amount of displacement is calculated from an image captured by a camera can also be adopted. In the present invention, the above-described encoder, laser, and camera are included in a sensor that detects friction.

Figure 11:
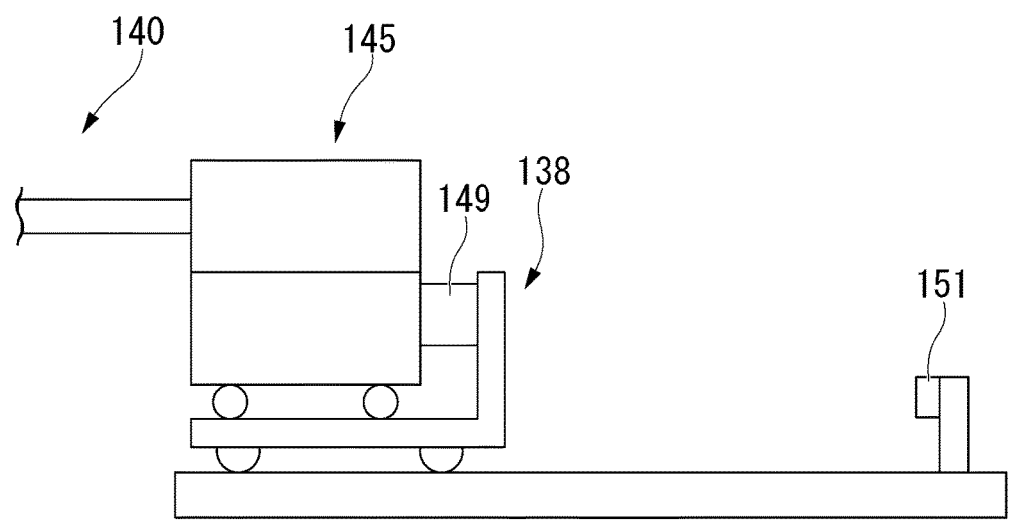
FIG. 11 is a view showing a part of a modification of the medical manipulator system.

Further, as shown in a modified example shown in FIG. 11, a speed sensor 151 for detecting the moving speed of the motor unit 145 may be further provided. In this case, the velocity component can be removed from the detection value of the force sensor 149 based on the detection value of the velocity sensor 151. As a result, the accuracy of the acquired friction parameter can be improved. Furthermore, since the friction parameter can be acquired even during the advancing/retracting operation of the treatment tool unit 140, the timing at which the correction amount can be calculated again can be increased.

It is natural that the above-described speed sensor may be combined with the system of the first embodiment or the modification shown in FIGS. 10A and 10B.

A third embodiment of the present invention will be described with reference to FIG. 12. The present embodiment is different from the above-described embodiments in the arrangement of the friction detection portion.

Figure 12:
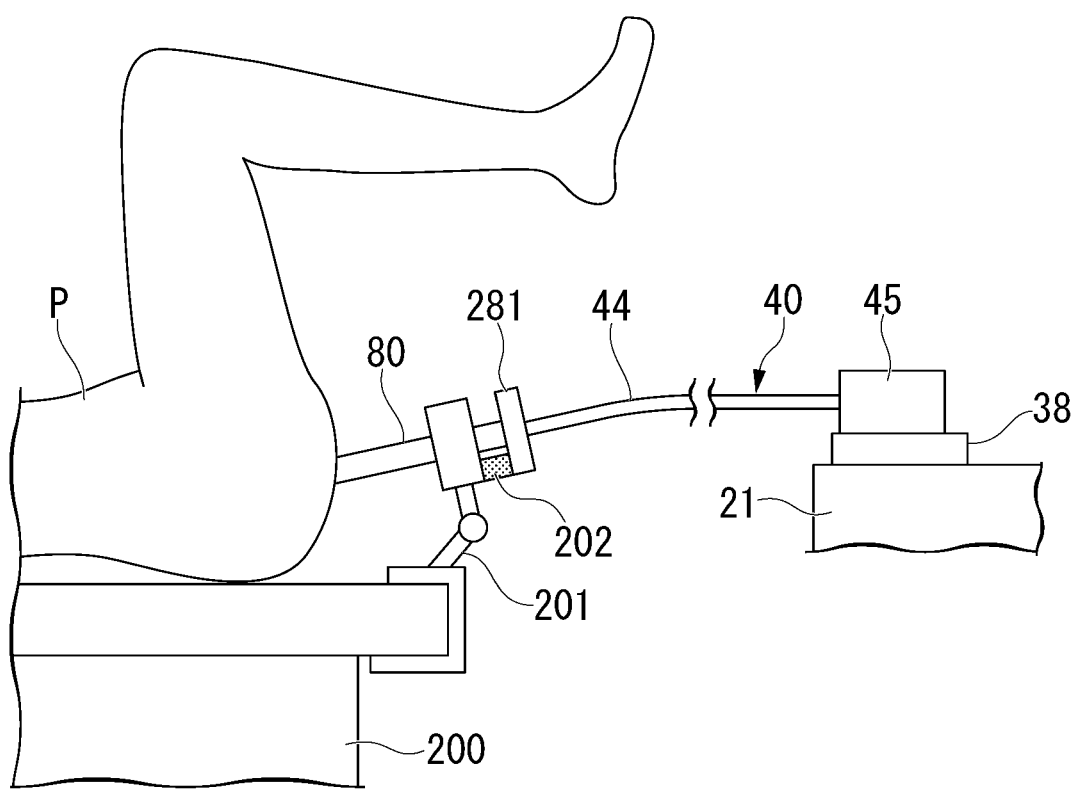
FIG. 12 is a schematic view showing a partial configuration of a medical manipulator system according to a third embodiment of the present invention.

FIG. 12 is a schematic view showing a partial configuration of a system according to the present embodiment. The proximal end of the overtube 80 is held by a holder 201 fixed to the operating table 200 on which the patient P lies. A flange 281 is provided at the proximal end of the overtube 80, and a force sensor 202 that functions as a friction detection portion is disposed at a position at which it is sandwiched between the flange 281 and the holder 201.

The connection portion 44 and the motor unit 45 are connected so as not to move relative to each other as in the second embodiment. The motor unit 45 is mounted on the mounting portion 38 so as not to move relative to the mounting portion 38. The force sensor 202 is logically connected to the calculation portion 36.

The operation at the time of use of the system of the present embodiment configured as described above will be described.

The preparation operation is substantially the same as in the first embodiment.

In step S110, when friction occurs between the connection portion 44 and the second lumen, an advancing force acts on the overtube 80 frictionally engaged with the connection portion 44 as the connection portion 44 is advanced. As a result, the force sensor 202 is pressed by the flange 281 and pressed against the holder 201, and the force sensor 202 receives a pressing force. The pressing force is detected by the force sensor 149.

In the friction parameter acquisition step of step S120, the detection value of the force sensor 202 is acquired instead of the detection value of the strain sensor 46. The subsequent flow is the same as in the first embodiment.

Also according to the system of the present embodiment, as in the first embodiment, even if the overtube 80 is curved or meanders in the body of the patient P, the arm portion 43 can be operated with responsiveness to the operation of the console 21 by the operator Op.

Further, since the force sensor 202 that functions as a friction detection portion is provided outside the motor unit 45, the effects described in the second embodiment can be similarly achieved.

Although embodiments of the present invention were described above, the technical scope of the present invention is not limited to the above-described embodiments. It is possible to change the combination of the components, to add various changes to each component, or to delete the combination in the range which does not deviate from the meaning of the present invention.

For example, the medical manipulator in the present invention is not limited to one performing control similar to that described above. For example, it may be a master-slave type medical manipulator provided with a master arm having a shape different from that of the arm portion.

Also, in the present invention, the end effector is not limited to the treatment tool. For example, it may be an imaging mechanism for magnifying and observing a part of the target site.

What is claimed is:

1. A medical manipulator system comprising:
   a treatment tool comprising an arm, an end effector arranged to the arm and a flexible elongated tube arranged proximally of the arm;
   an actuator configured to generate a drive force for driving one or more of the arm and the end effector;
   a detector configured to detect a force parameter; and
   a controller configured to:
   generate an operation signal for operating the actuator to generate the drive force;

calculate, based on the force parameter detected, a friction generated between an outer surface of the flexible elongated tube and an inner surface of an overtube; and calculate a correction amount for adjusting the operation signal based on the friction calculated.

2. The medical manipulator system according to claim 1, wherein the actuator is arranged in a housing arranged to a proximal end of the treatment tool, and
wherein the detector is arranged to the housing.

3. The medical manipulator system according to claim 1, further comprising:
a housing arranged to the detector; and
a mounting portion configured to advance and retreat the housing relative to the overtube,
wherein the housing and the mounting portion are connected by the detector, and
wherein the detector is configured to detect the force parameter as the mounting portion advances and retreats the housing relative to the overtube as the friction is generated between the outer surface of the flexible elongated tube and the inner surface of the overtube.

4. The medical manipulator system according to claim 3, further comprising:
a speed sensor configured to detect a moving speed of the housing connected to the mounting portion,
wherein the controller is configured to calculate the correction amount based on the friction calculated and the moving speed detected.

5. A method for operating a medical manipulator system comprising:
a treatment tool comprising an arm, an end effector arranged to the arm and a flexible elongated tube arranged proximally of the arm;
an actuator configured to generate a drive force for driving one or more of the arm and the end effector; and
a detector configured to detect a force parameter,
wherein the method comprises:
generating an operation signal for operating the actuator to generate the drive force;
calculating, based on the force parameter detected, a friction generated between an outer surface of the flexible elongated tube and an inner surface of an overtube; and
calculating a correction amount for adjusting the operation signal based on the friction calculated.

6. The medical manipulator system according to claim 2, wherein the detector is held between an inside of the housing and a proximal end of the flexible elongated tube.

7. The medical manipulator system according to claim 1, further comprising:
a mounting holder,
wherein the detector is disposed between the mounting holder and a flange.

8. The medical manipulator system according to claim 1, wherein the detector comprises a spring, and
wherein the force parameter corresponds to a displacement amount of the spring.

9. The medical manipulator system according to claim 1, wherein the detector comprises a strain sensor, and
wherein the force parameter corresponds to a strain.

10. The medical manipulator system according to claim 1, wherein the force parameter changes in accordance with a total bending angle of the flexible elongated tube.

11. The medical manipulator system according to claim 1, wherein the controller is configured to calculate the friction by referring to a table that associates the force parameter detected and the friction.

12. The medical manipulator system according to claim 1, wherein the controller is configured to calculate the correction amount by referring to a table that associates the friction calculated and the correction amount.

13. The method according to claim 5, wherein the actuator is arranged in a housing arranged to a proximal end of the treatment tool, and
wherein the detector is arranged to the housing.

14. The method according to claim 5, wherein the medical manipulator system further comprises:
a housing arranged to the detector;
a mounting portion configured to advance and retreat the housing relative to the overtube;
wherein the housing and the mounting portion are connected by the detector, and
wherein the detector is configured to detect the force parameter as the mounting point advances and retreats the housing relative to the overtube as the friction is generated between the outer surface of the flexible elongated tube and the inner surface of the overtube; and
a speed sensor configured to detect a moving speed of the housing connected to the mounting portion, and
wherein calculating the correction amount comprises calculating the correction amount based on the friction calculated and the moving speed detected.

15. The method according to claim 5, wherein the actuator is arranged in a housing arranged to a proximal end of the treatment tool, and
wherein the detector is held between an inside of the housing and a proximal end of the flexible elongated tube.

16. The method according to claim 5, wherein the medical manipulator system further comprises a mounting holder, and
wherein the detector is disposed between the mounting holder and a flange.

17. The method according to claim 5 wherein the detector comprises a spring, and
wherein the force parameter corresponds to a displacement amount of the spring.

18. The method according to claim 5, wherein the force parameter corresponds to a strain.

19. The method according to claim 5, wherein the force parameter changes in accordance with a total bending angle of the flexible elongated tube.

20. The method according to claim 5, wherein calculating the friction comprises calculating the friction by referring to a table that associates the force parameter detected and the friction, and
wherein calculating the correction amount comprises calculating the correction amount by referring to a table that associates the friction calculated and the correction amount.

* * * * *